(12) United States Patent
Hesketh et al.

(10) Patent No.: US 8,718,956 B2
(45) Date of Patent: May 6, 2014

(54) HIGH-PRESSURE QUARTZ CRYSTAL MICROBALANCE

(75) Inventors: Peter Hesketh, Atlanta, GA (US); Sankar Nair, Atlanta, GA (US); Ken McCarley, Bartlesville, OK (US); Milad Navaei, Atlanta, GA (US); Kevin Bagnall, Bartlesville, OK (US); Anandram Venkatasubramanian, Atlanta, GA (US)

(73) Assignees: Phillip 66 Company, Houston, TX (US); Georgia Tech Research Corporation, Atlanta, GA (US)

( * ) Notice: Subject to any disclaimer, the term of this patent is extended or adjusted under 35 U.S.C. 154(b) by 329 days.

(21) Appl. No.: 13/208,842

(22) Filed: Aug. 12, 2011

(65) Prior Publication Data

US 2012/0078541 A1 Mar. 29, 2012

Related U.S. Application Data

(60) Provisional application No. 61/387,942, filed on Sep. 29, 2010.

(51) Int. Cl.
| G01N 11/00 | (2006.01) |
| G06F 19/00 | (2011.01) |
| G01N 5/02 | (2006.01) |
| G01N 15/08 | (2006.01) |

(52) U.S. Cl.
CPC ............... *G01N 5/02* (2013.01); *G01N 15/082* (2013.01); *G01N 15/0893* (2013.01)
USPC ............. 702/50; 73/23.34; 73/865.8; 702/98; 702/99

(58) Field of Classification Search
CPC ... G01N 5/02; G01N 15/082; G01N 15/0893; G01N 17/008; G01G 3/13; G01G 3/16
USPC .......... 702/45, 47, 50, 130, 131, 138, 98, 99; 73/19.03, 23.35, 24.06, 865.8, 23.24; 156/345.24; 177/210 FP; 422/82.01
See application file for complete search history.

(56) References Cited

U.S. PATENT DOCUMENTS

| 6,370,939 B2 | 4/2002 | Smith et al. |
| 6,544,478 B1 | 4/2003 | Oyama et al. |
| 7,036,375 B2 | 5/2006 | Nozaki |
| 7,285,736 B2 | 10/2007 | Korpi |
| 2008/0236747 A1 | 10/2008 | Matsudo et al. |
| 2009/0211335 A1 | 8/2009 | Jovancicevic et al. |
| 2009/0293590 A1 | 12/2009 | Zeng et al. |

FOREIGN PATENT DOCUMENTS

| WO | WO2008121446 | 10/2008 |
| WO | WO2009108825 | 9/2009 |
| WO | WO2009128636 | 10/2009 |
| WO | PCT/US11/47578 | 8/2011 |

*Primary Examiner* — John H Le
(74) *Attorney, Agent, or Firm* — Gardere Wynne Sewell LLP; Chris P. Perque; Teresa J. Lechner-Fish

(57) ABSTRACT

Described is an apparatus for measuring mass change under high pressure, comprising: a high pressure cell comprising a reference quartz crystal microbalance sensor and a sample quartz crystal microbalance sensor, wherein the sample quartz crystal microbalance sensor is coated with a test sample selected from the group consisting of nanoporous materials and metal-organic frameworks; a pressure sensor operatively connected to the high pressure cell; a thermocouple operatively connected to the high pressure cell, wherein the high pressure cell is maintained at a pre-selected temperature; a gas inlet fluidly connected to the high pressure cell; and a gas outlet fluidly connected to the high pressure cell. Also described are methods of making and using the apparatus.

22 Claims, 16 Drawing Sheets

SCHEMATIC OF DEVICE

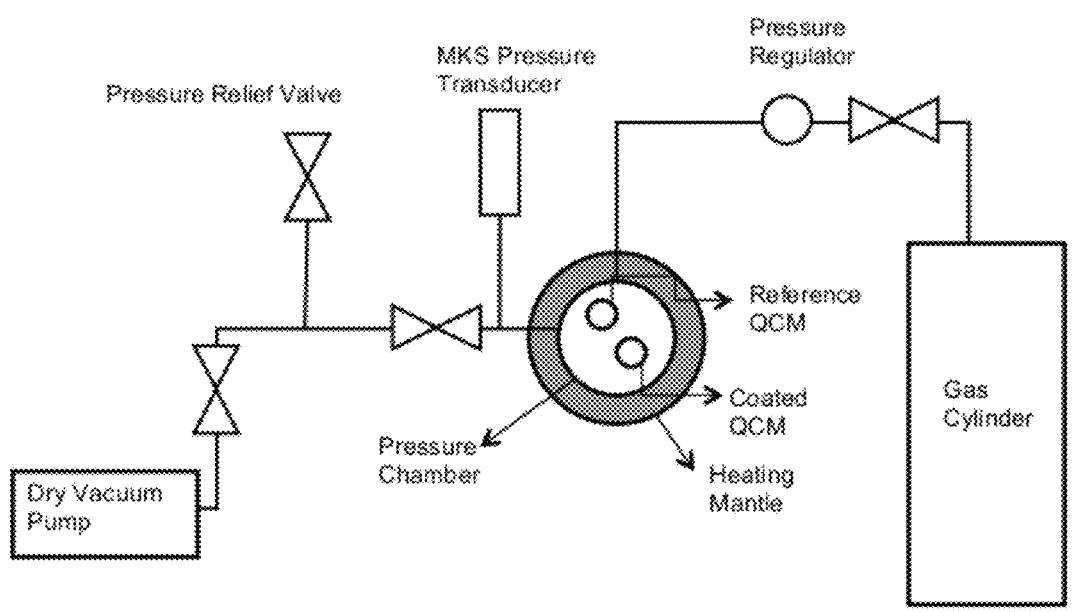
FIG. 1: SCHEMATIC OF DEVICE

FIG. 2A: SEM images of CuBTC MOF deposited on QCM
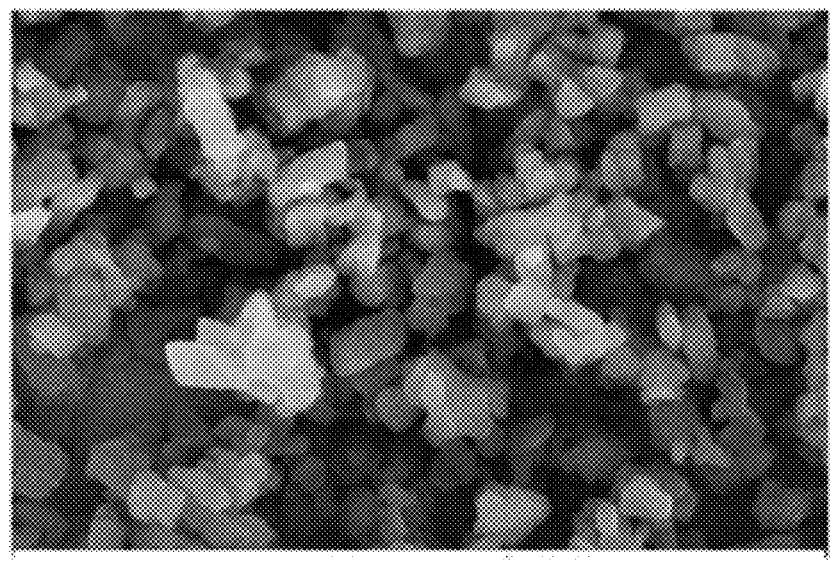
FIG. 2B: SEM images of CuBTC MOF deposited on QCM

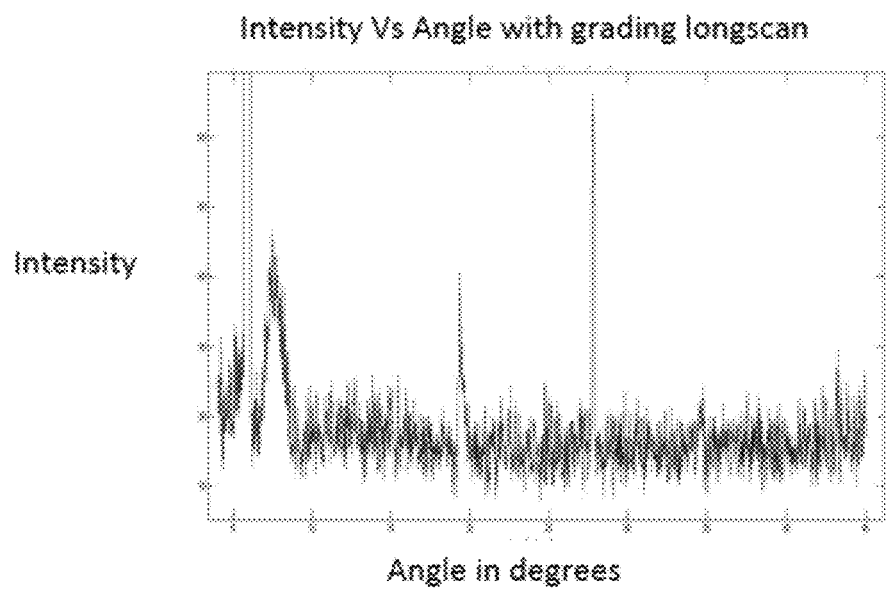
FIG. 2C: XRD Pattern of CuBTC deposited on the QCM
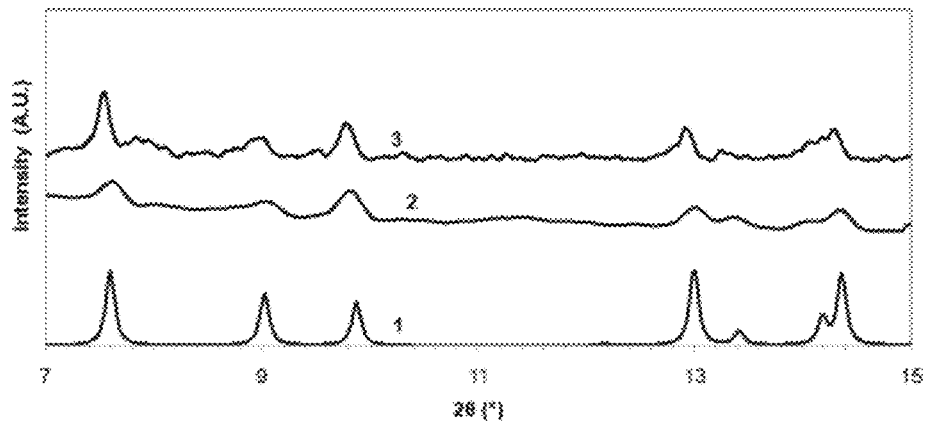
FIG. 2D: XRD patterns of Cu-hifbb MOF crystals deposited on the QCM. Before (2) and after experiment (3) and simulated patterns (1)

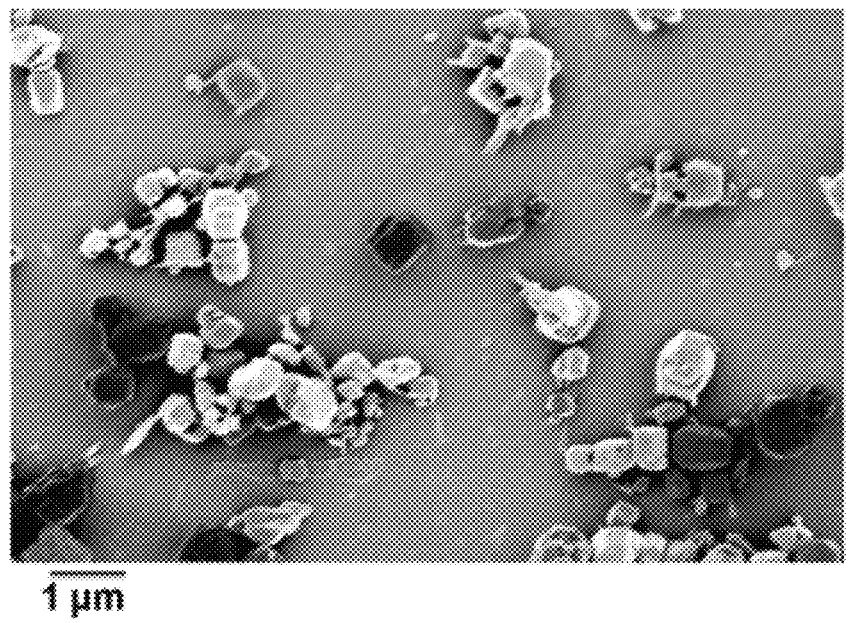
FIG. 2E: SEM images of Cu-hfipbb crystals deposited on the QCM surface
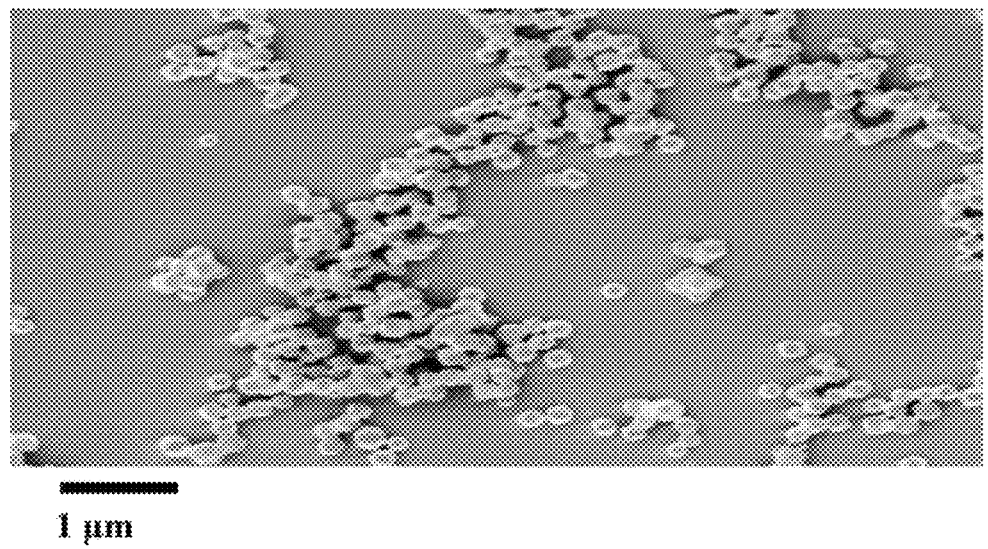
FIG. 2F: SEM image of ZIF 90 crystals deposited on the QCM surface

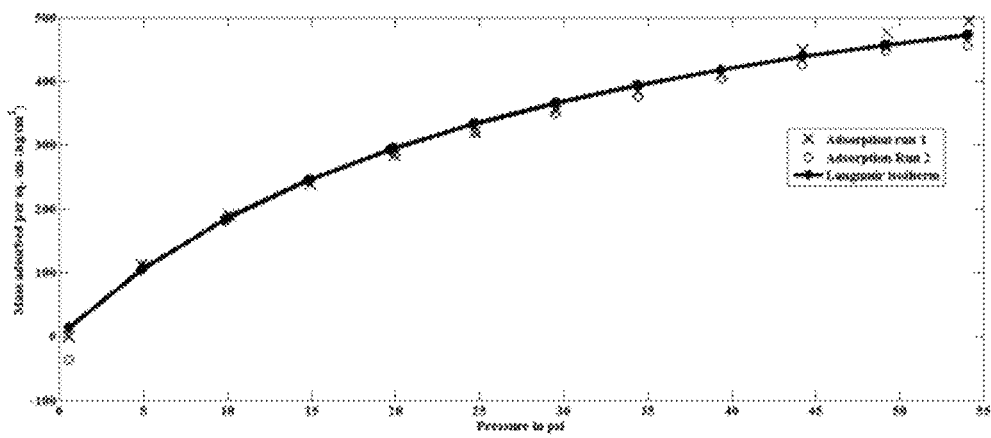
FIG. 3A: Comparison of experimental observations with langmuir isotherm of HKUST-1 for $CO_2$ at 21°C

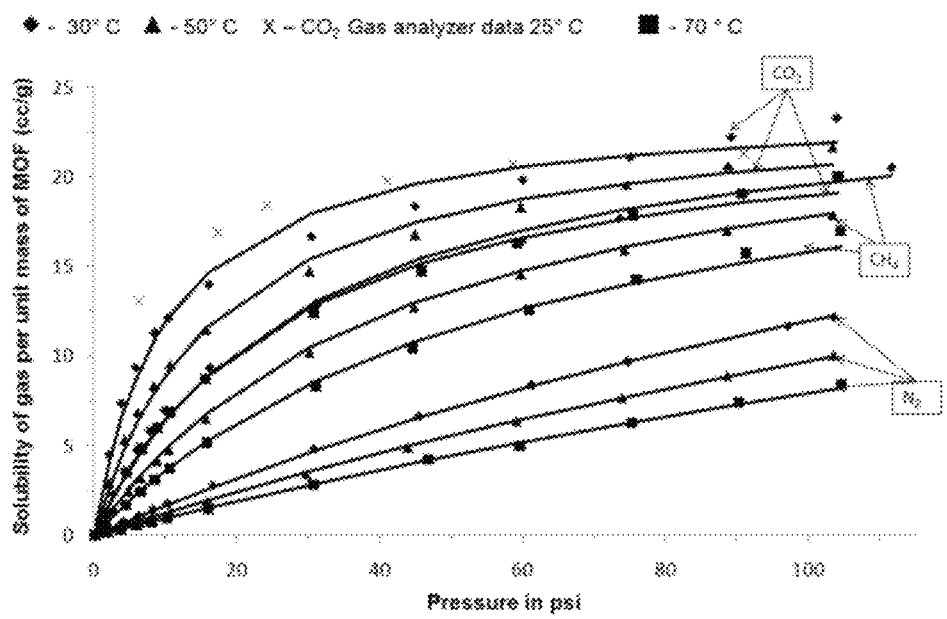
FIG. 3B: Comparison of experimental isotherms with Langmuir isotherm
for $CO_2$, $N_2$ and $CH_4$ for Cu-hfbb at different temperatures

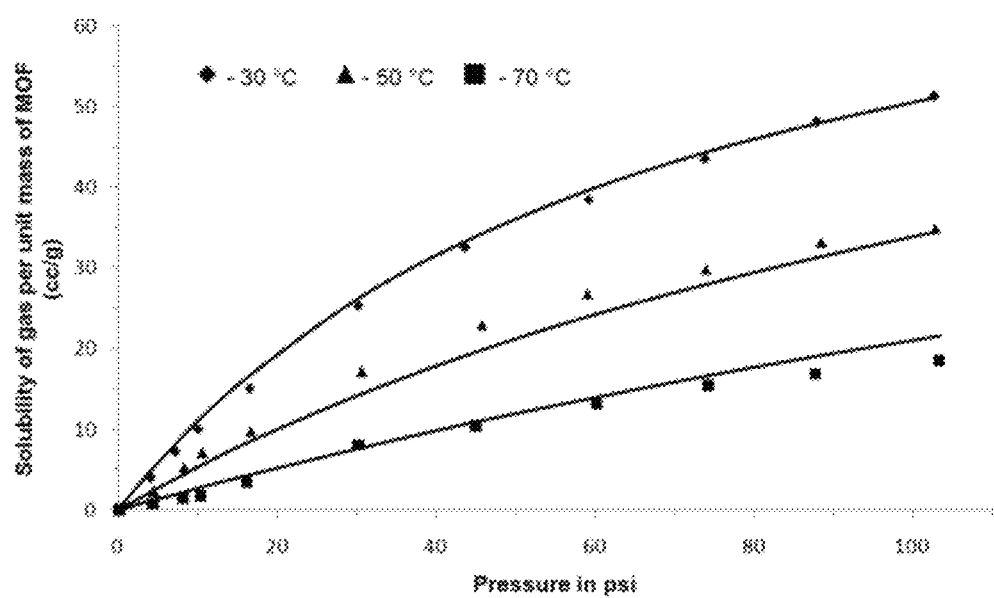
FIG. 3C: Comparison of experimental isotherms with Langmuir isotherm
for $CO_2$ for ZIF 90 at different temperatures

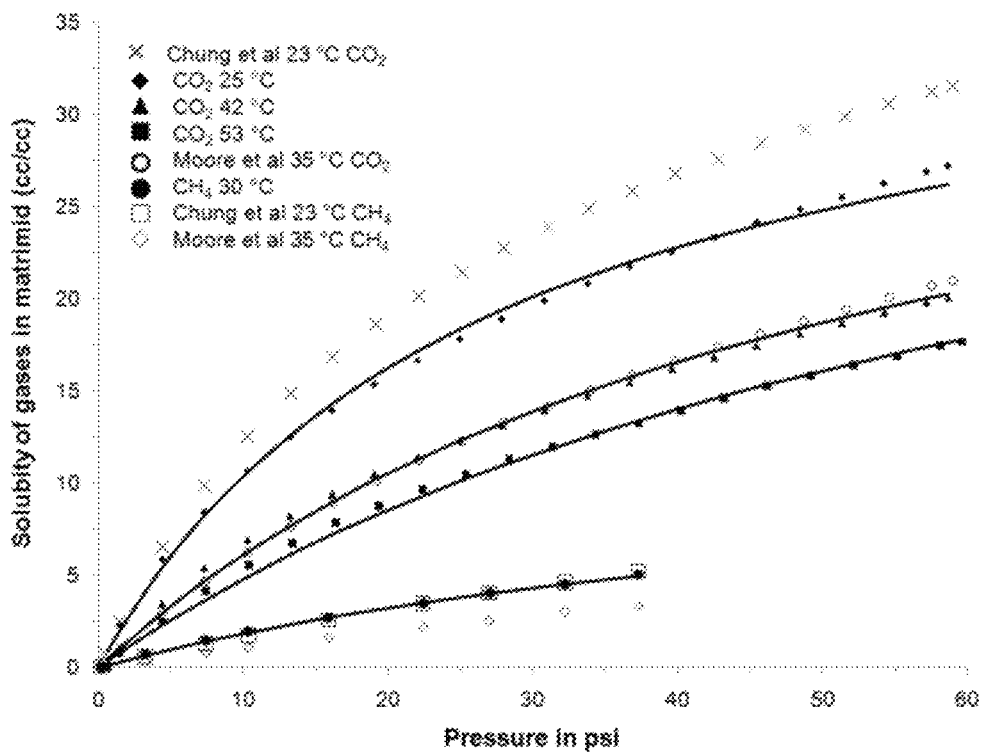
FIG. 3D: Comparison of experimental adsorption isotherms (as in the legends) with langmuir isotherms (solid lines) with the data available in the literature for different gases in Matrimid 5218

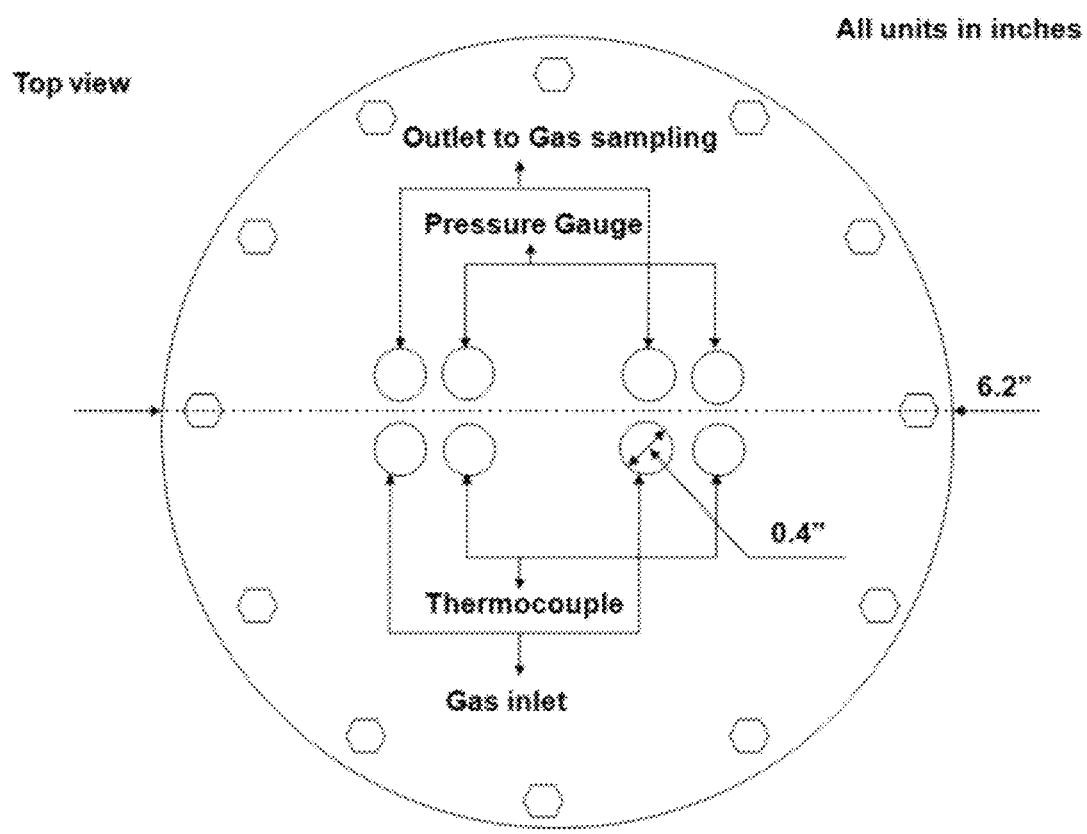
FIG. 5A Schematic Diagram of the Chamber Head

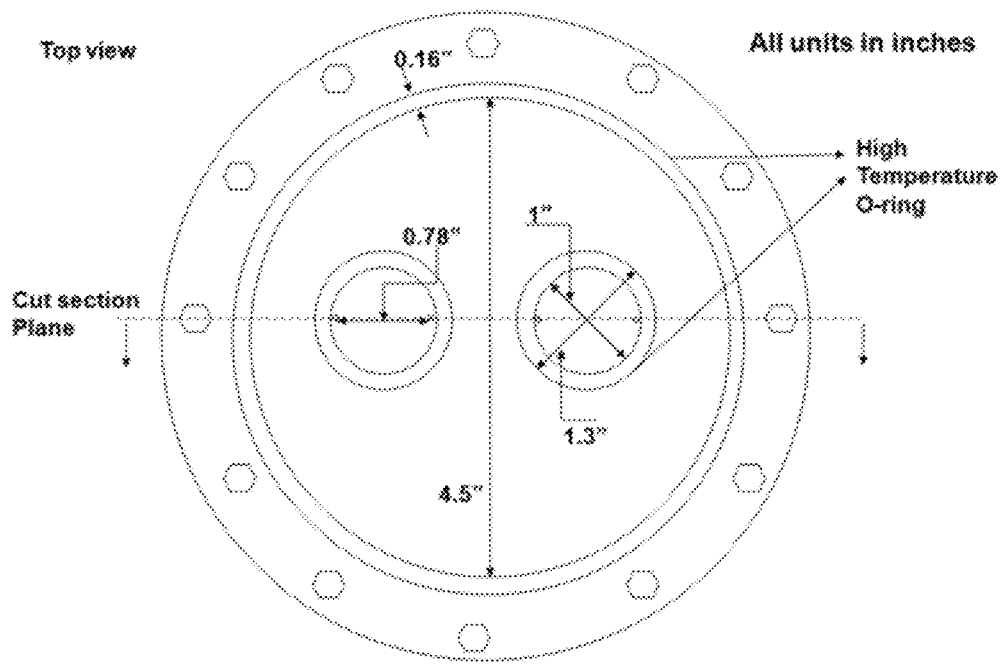
FIG. 5B Schematic View of the Chamber Bottom
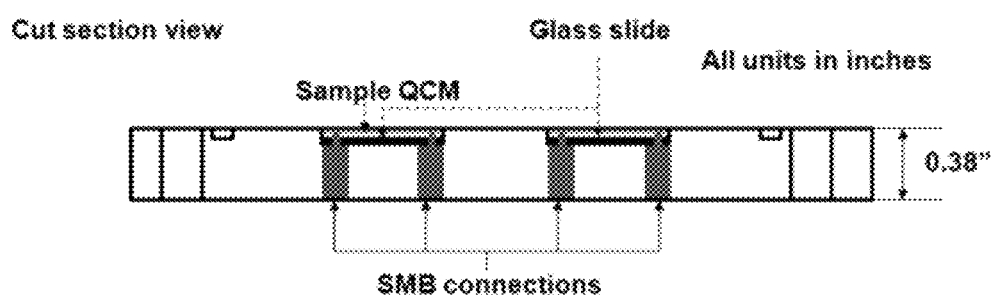
FIG. 5C Schematic Diagram of the Cut Section View of the Chamber Bottom

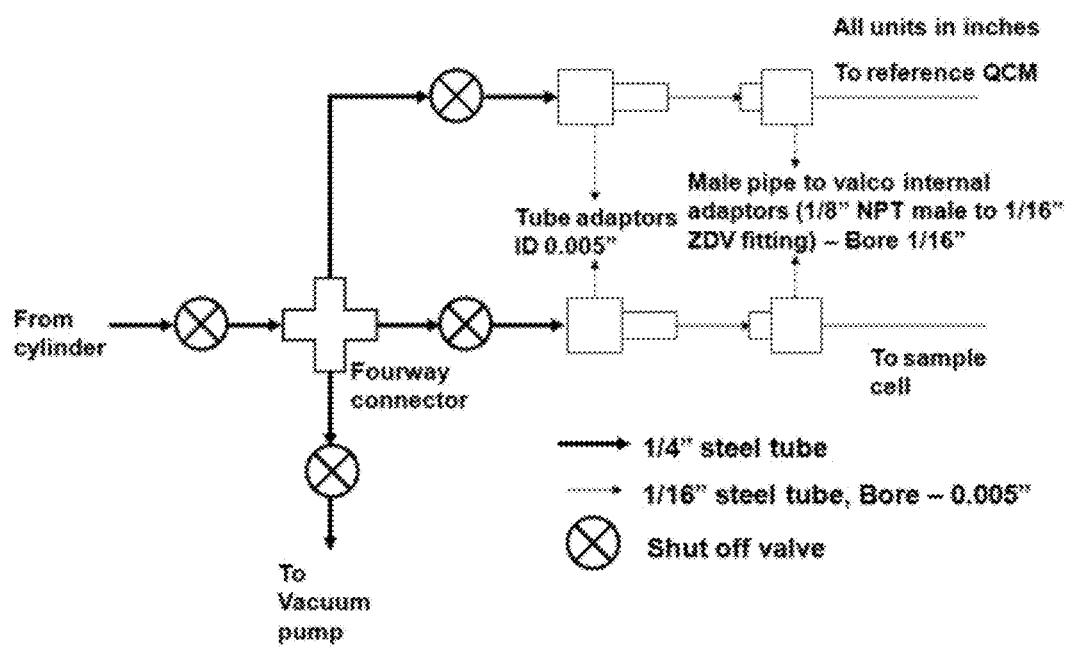
FIG. 6A Schematic Diagram of the Gas feed system for the Binary Gas QCM based Adsorption setup

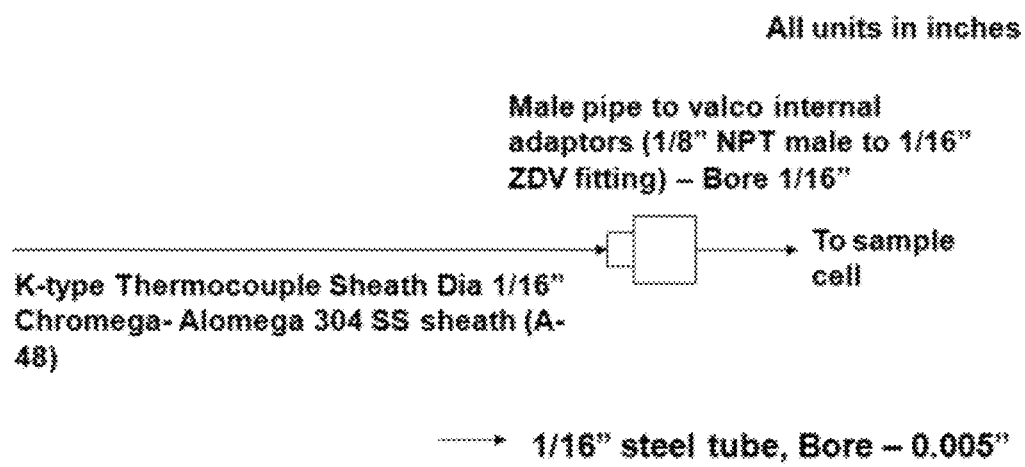
FIG. 6B Schematic Diagram of the Temperature measurement module

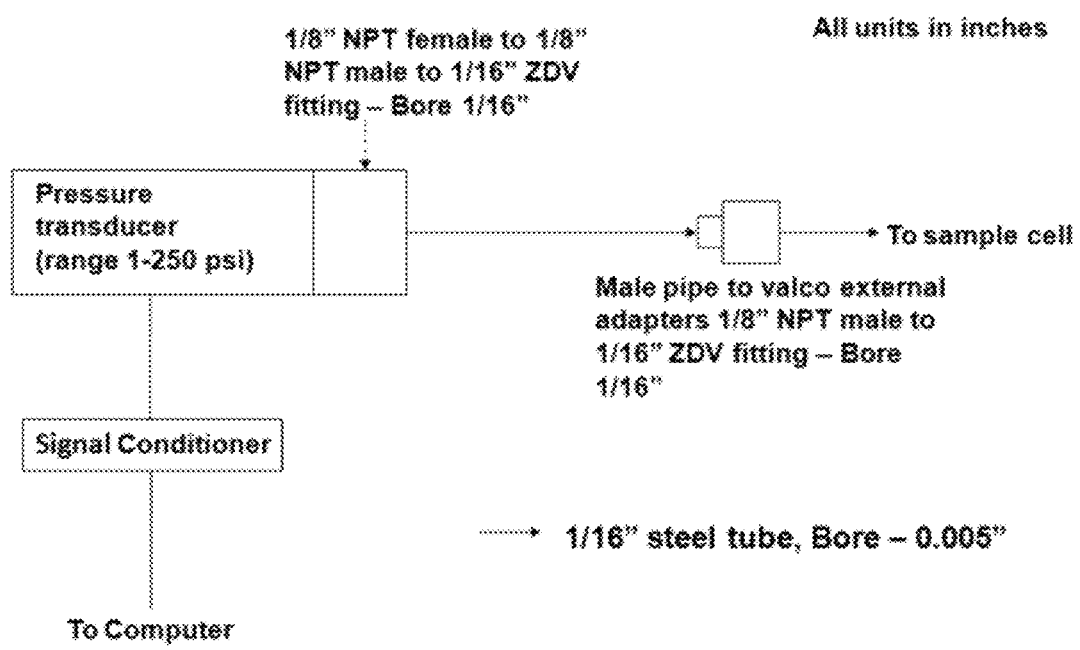
FIG. 6C Schematic View of the Pressure Measurement Module

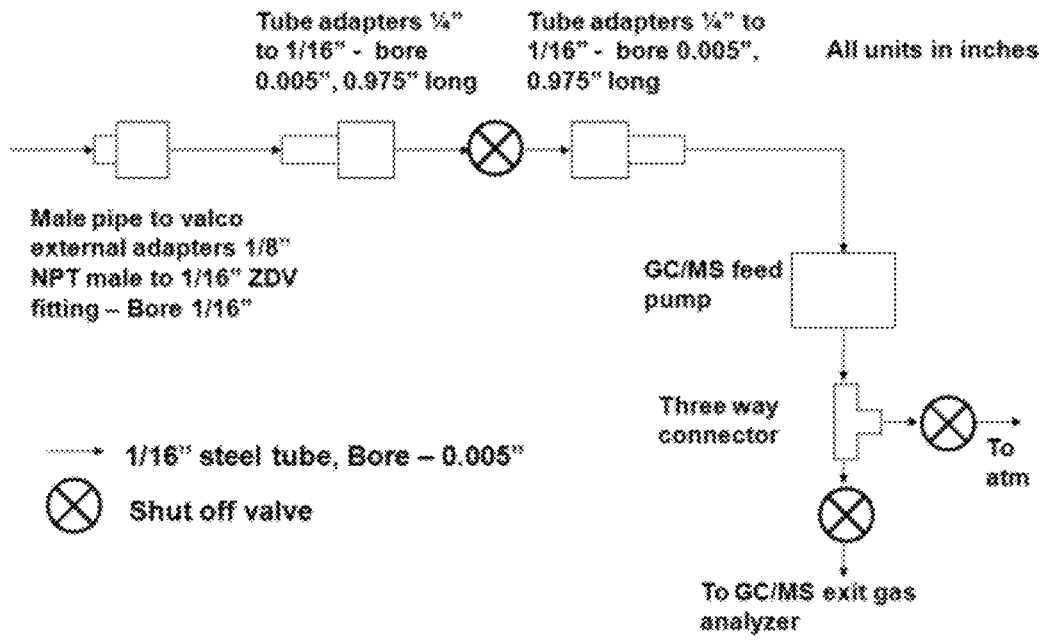
Fig. 6D Schematic representation of the Exit gas analyzer module connecting the sample chamber to the GC/MS set up
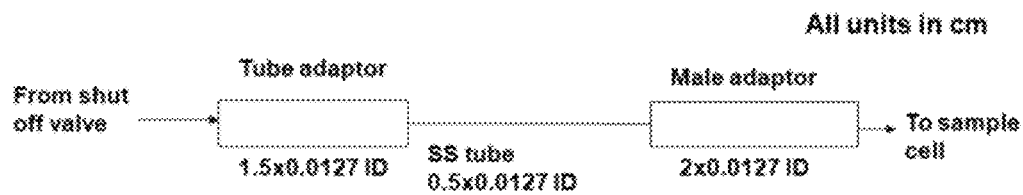
FIG. 6E Detailed schematic view of the Gas Feed valve fittings to connect the sample chamber to the dosing gas cylinder

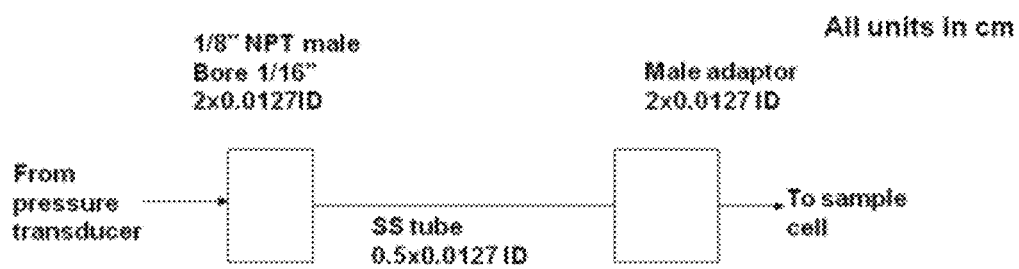
FIG. 6F Detailed schematic view of the Pressure gauge fittings between the sample chamber and Pressure Transducer
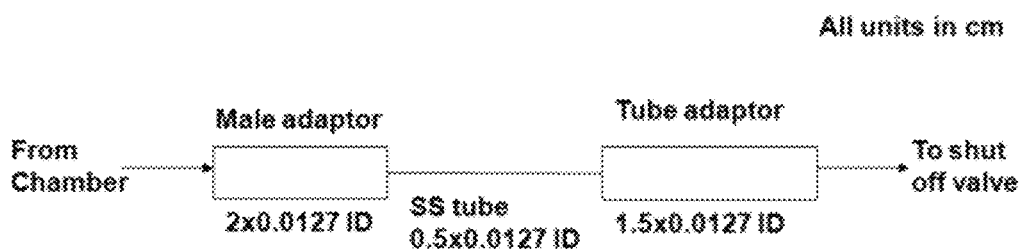
FIG. 6G Detailed Schematic view of the Exit gas analyzer fitting to connecting the sample chamber to first shut off valve downstream.

HIGH-PRESSURE QUARTZ CRYSTAL MICROBALANCE

CROSS-REFERENCE TO RELATED APPLICATIONS

This application claims priority to U.S. application 61/387,942, filed Sep. 29, 2010 and incorporated by reference in its entirety.

FEDERALLY SPONSORED RESEARCH STATEMENT

Not applicable.

FIELD OF THE INVENTION

The invention relates to a high-pressure quartz crystal microbalance for measuring gas adsorption and diffusion on nanoporous materials and thin films and the like.

BACKGROUND OF THE INVENTION

Metal-Organic Frameworks (MOFs) are crystalline compounds consisting of metal ions or clusters coordinated to often rigid organic molecules to form one-, two-, or three-dimensional structures that can be porous. In some cases, the pores are stable to elimination of the guest molecules (often solvents) and can be used for the storage of gases such as hydrogen and carbon dioxide. Other possible applications of MOFs are gas purification, gas separation, catalysis and sensors.

With the emergence and development of new materials, such as nanotubes or MOFs, it is important to determine the gas adsorption characteristics of these materials, especially under high pressure and/or in a gas mixture. The characterization of gas adsorption in porous materials is performed predominantly by commercial gravimetric equipment. However, their capital and operating costs are generally high. Furthermore, they require relatively large amounts of sample (typically >100 mg) to obtain accurate data, and also cannot measure gas adsorption in thin films or coatings. It is therefore desirable to broaden the range of techniques that can be used to reliable measure the adsorption properties of MOF materials over a substantial range of pressure and temperature by non-gravimetric methods, ideally with only a small sample size requirement (<1 mg), and with the sample being potentially in powder, coating, or thin film form. The ability to measure the gas adsorption and desorption characteristics of thin films and coatings, or very small amounts of sample, under high pressure and temperature, and/or in an environment containing more than one gas, is desirable because that is usually the real conditions under which the thin films/membranes/coatings are to be used.

Quartz is one member of a family of crystals that experience the piezoelectric effect—the charge that accumulates in certain solid materials (notably crystals, certain ceramics, and biological matter such as bone, DNA and various proteins) in response to applied mechanical strain. The piezoelectric effect has found applications in high power sources, sensors, actuators, frequency standards, motors, etc., and the relationship between applied voltage and mechanical deformation is well known, and allows probing of acoustic resonance by electrical means.

A quartz crystal microbalance commonly referred to as a "QCM", measures a mass per unit area by measuring the change in frequency of such a quartz crystal resonator. The resonance is disturbed by the addition or removal of a small mass due to oxide growth/decay or film deposition at the surface of the acoustic resonator. The QCM can be used under vacuum, in gas phase, and more recently in liquid environments. Frequency measurements are easily made to high precision. In addition to measuring the frequency, the dissipation is often measured to help analysis. The dissipation is a parameter quantifying the damping in the system, and is related to the sample's viscoelastic properties. Other advantages of QCM over conventional gravimetric devices are that it is compact and simple for system set-up, stable for in situ measurements (no buoyancy effect), and exquisitely sensitive.

Although highly sensitive, the QCM has not been typically used in high pressure environments because pressure changes affect the frequency of oscillation, thus complicating interpretation of the measurements. Also, quartz can be brittle and may crack under shock or sudden changes in pressure. WO2009108825 discloses a high pressure QCM, but the device therein has only a single QCM in the high pressure chamber, and thus suffers from the problem of accurate calibration for quantitatively correct measurements of adsorption. The response to temperature and pressure has to be first evaluated without the presence of analyte, and then repeated under identical conditions with analyte present. However, the reproducibility in setting the temperature and pressure can complicate interpretation of the data. Therefore, the apparatus described in the patent WO2009108825 can only provide qualitatively correct data.

U.S. Pat. No. 7,036,375 uses a plurality of piezoelectric transducers, as does the art referenced therein, wherein each of the transducers can have two oscillating domains, one used as a reference and the other being used as a target oscillating domain for measurement of a sample. See also U.S. Pat. No. 6,544,478. However, in these patents the devices are multi-channel QCM sensors designed to allow measurement of more than one sample at a time and do not relate to high pressure QCMs. Furthermore, these QCM sensor arrays operate close to room temperature in an aqueous environment for the detection of adsorbed biomolecules. The presently described device has been tested to operate at a range of temperatures from room temperature to about 185° C. under low vacuum, and under gas environments from room temperature to 120° C. for pressures tested up to 8.25 atm so far.

Therefore, there is a need for a better apparatus capable of measuring the adsorption and desorption characteristics of a material under high pressure and/or in an environment of one or more gases.

SUMMARY OF THE INVENTION

Generally speaking, the invention is directed to a high pressure QCM having high pressure couplings to allow materials to be measured at high pressures. In order to improve the accuracy and reliability of the device, several features are added, including temperature and pressure sensors to accurately ascertain these important parameters, and a gas meter to accurately control gas influx into the high pressure cell.

Two QCM are used—a reference and a sample QCM. Thus, one crystal responds to the pressure and temperature changes, while the other one responds to the pressure, temperature and presence of the analyte and subtraction can yield data related to analyte only.

Metered gas amounts are allowed to enter the cell and equilibrate, and then measurements are taken, and this cycle is repeated. Both temperate and pressure changes are accounted for and the use of multiple measurements allows accurate determinations of mass change, even at high pressures and temperatures. If more than one gas is to be measured at a time, the device can be combined with any gas identification/quantification device, in order to sample the composition of the exiting gas. With this device, the adsorption of gases in thin films of nanoporous and microporous materials can be measured under realistic conditions.

According to an aspect of the present invention, there is provided an apparatus for measuring mass change under high pressure, and the apparatus comprises: a high pressure cell comprising a reference quartz crystal microbalance sensor and a sample quartz crystal microbalance sensor, the sample quartz crystal microbalance sensor being coated with a test sample; a pressure sensor operatively connected to the high pressure cell; a thermocouple operatively connected to the high pressure cell; a gas inlet fluidly connected to the high pressure cell; and a gas outlet fluidly connected to the high pressure cell.

In one embodiment, an identification means, for example an FTIR, GC, MS, GC/MS, HPLC, or similar instrument that can identify the desorbed gas or gases, is connected to the gas outlet to determine the identity (and/or amount) of gas within the high pressure cell. In another embodiment, a volume controlling means, for example a flow meter, is connected to the gas inlet to control the amount of gas being introduced into the high pressure cell.

According to another aspect of the present invention, there is provided a method for measuring gas adsorption under high pressure. The method comprises the steps of: providing an apparatus comprising a high pressure cell comprising a reference quartz crystal microbalance sensor and a sample quartz crystal microbalance sensor, the sample quartz crystal microbalance sensor being coated with a test sample; a pressure sensor connected to the high pressure cell; a thermocouple connected to the high pressure cell; a gas inlet connected to the high pressure cell; and a gas outlet connected to the high pressure cell, wherein the high pressure cell is maintained at a pre-selected temperature; measuring, at a first state, a first temperature from the thermocouple and a first pressure from the pressure sensor; measuring, at the first state, a first reference resonant frequency from the reference quartz crystal microbalance sensor and a first sample resonant frequency from the sample quartz crystal microbalance sensor; introducing a gas to the high pressure cell through the gas inlet at the pre-selected temperature; measuring, at a second state, a second temperature from the thermocouple and a second pressure from the pressure sensor; measuring, at the second state, a second reference resonant frequency from the reference quartz crystal microbalance sensor and a second sample resonant frequency from the sample quartz crystal microbalance sensor; and determining a mass of the gas adsorbed to the test sample coated to the sample quartz crystal microbalance sensor based on mass difference between the reference resonant frequency and the sample resonant frequency.

In one embodiment, the test sample coated to the sample QCM sensor is, for example, a nanoporous material, MOF or a thin film. The nanoporous material can be any metal organic framework or gas adsorbing material, such as CuBTC, Cu-hifbb, ZIF 90 crystal, $Zn_4O(BTB)_2$, $Zn_4O(BDC)_3$, $Mn_3[(Mn_4Cl)_3(BTT)_8]_2$, or $Cu_3(BTC)_2(H_2O)_3$.

In one embodiment, the gas introduced to the high pressure cell comprises two or more component gases, such as $H_2$, $CH_4$, $CO_2$, $CO$, $H_2O$, $N_2$, $O_2$, and other small gases. In another embodiment, the high pressure cell has a small cell volume, and a gas identification means, for example a GC/MS, is connected to the gas outlet for determining the identity of one or more gases within the high pressure cell.

The use of the word "a" or "an" when used in conjunction with the term "comprising" in the claims or the specification means one or more than one, unless the context dictates otherwise.

The term "about" means the stated value plus or minus the typical margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, a "nanoporous material" indicates a porous material having pores essentially in the 1-100 nanometer range.

A "thin film" indicates a material deposited onto the quartz crystal microbalance sensor. Thickness is variable, ranging from a few nanometers to 100 microns.

"High pressure" indicates a pressure larger than one atmosphere.

The following abbreviations are used herein:

| | |
|---|---|
| $BDC^{2-}$ | 1,4-benzenedicarboxylate (MOF-5) |
| BNC connector | Bayonet Neill-Concelman connector |
| $BTB^{3-}$ | 1,3,5-benzenetribenzoate (MOF-177) |
| $BTC^{3-}$ | 1,3,5-benzenetricarboxylate (CuBTC) |
| CuBTC, also HKUST-1 | $Cu_3(BTC)_2(H_2O)$ |
| Cu-hfipbb | $Cu(hfipbb)(H_2hfipbb)_{0.5}$ |
| FTIR | Fourier transform infrared spectroscopy |
| GC | gas chromatography |
| $H_3BTC$ | 1,3,5-benzenetricarboxylic acid |
| $H_3BTT$ | benzene-1,3,5-tris(1H-tetrazole) |
| hfipbb | 4,4'-hexafluoroisopropylidene-bis-benzoate |
| HPLC | high pressure liquid chromatography |
| MOF | metal organic framework |
| MS | mass spectrometery |
| QCM | quartz crystal microbalance |
| SEM | scanning electron micrograph |
| SMB | sub-miniature B |
| XRD | X-ray diffraction |
| ZIF-90 | Zeolitic imidazolate framework-90 |

BRIEF DESCRIPTION OF THE DRAWINGS

FIG. 1 is a schematic view of a single-component gas measurement device. The two QCM devices inside the high pressure chamber are not shown for simplicity.

FIG. 2A-2F show the SEM images of MOF materials (CuBTC, Cu-hfipbb, ZIF-90) coated on QCM and XRD patterns of these MOFs deposited on gold substrates.

FIG. 3A-3D show the experimental results of the present invention for 3 MOF materials and 1 polymer material, and fits of the data to the theoretical Langmuir isotherm in order to obtain the fundamental adsorption thermodynamic parameters of interest.

FIG. 5A-5C show the chamber head and chamber bottom of one high pressure cell of the present invention.

FIG. 6A-6G show the gas feed design, thermocouple fitting, pressure gauge fitting, exit gas analyzer, and the exemplified selection of tubes, bores and adaptors of one embodiment of the device shown in FIG. 4.

DESCRIPTION OF EMBODIMENTS OF THE INVENTION

Figure 4:
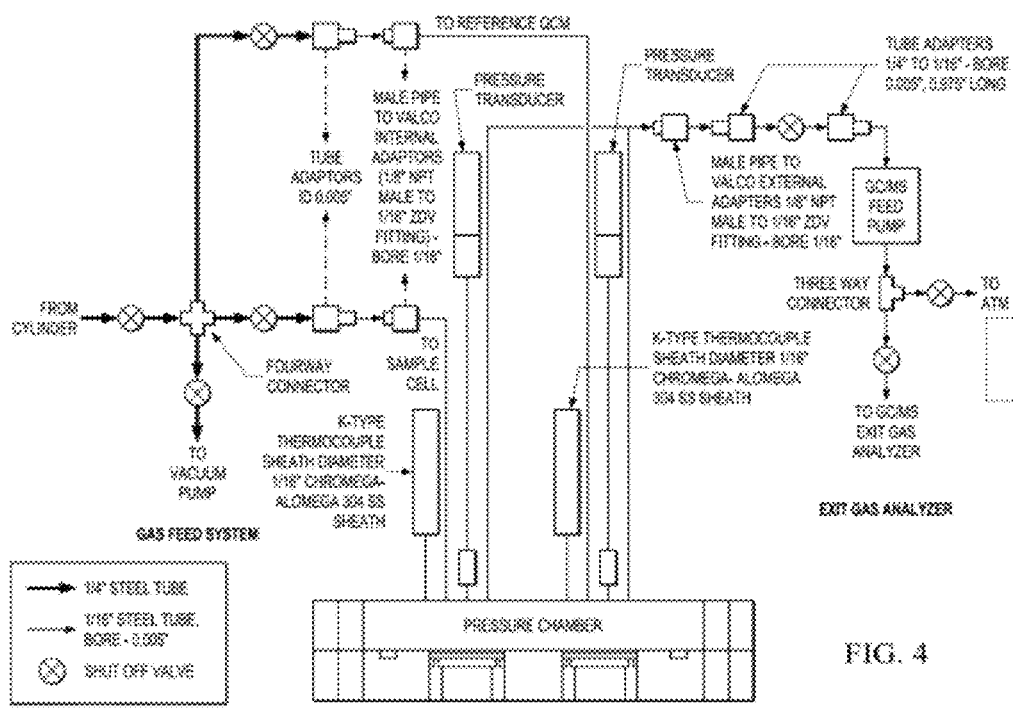
FIG. 4 shows the system and apparatus of the present invention that is used to detect a measure gas adsorption in a binary gas system. Additional detail regarding the prototype used in the experimental examples is available in FIGS. 5 and 6.

Metal organic frameworks (MOFs) are a rather new class of crystalline nanoporous materials with salient features such as tailorable nanoporosity, high surface area and analyte-specific adsorption. Among the well-known MOFs, we select three examples for testing the device of the invention:

Example 1A

HKUST-1 has the structure of formula $Cu_3(BTC)_2(H_2O)$ comprising a binuclear $Cu_2$ paddlewheel. Its structure consists of two types of "cages" and two types of "windows" separating these cages. Large cages (13.2 and 11.1 Angstrom in diameter) are interconnected by 9 Angstrom (Å) windows of square cross section. The large cages are also connected to tetrahedral shaped side pockets of roughly 6 Å through triangular shaped windows of about 4.6 Å.

Example 1B $Cu(hfipbb)(H_2hfipbb)_{0.5}$ is a crystalline interpenetrating framework containing ordered microporous 1D channels, built on a $Cu_2(hfipbb)_4(H_2hfipbb)_2$ paddle-wheel building unit. This MOF was selected because it has cages that are moderate in size relative to small gas molecules (~5.1 Å×5.1 Å) connected by small windows (~3.5 Å×3.2 Å).

Example 1C

The structure of as-synthesized ZIF-90 crystals was found to be related to the sodalite topology ($SiO_2$, sod A-C) by replacing the Si and O with Zn(II) and ICA links, respectively. This leads to an expanded ZIF structure with large voids (B) and an extended 3-D ZIF structure with an aperture of 3.5 Å in diameter and a pore size of 11.2 Å (C).

Example 1D

As an additional example, we also show measurements of adsorption data from a sample of a commercially available polymer (Matrimid®).

The above are used as exemplary MOF materials herein in order to measure the absorption of gases into the porous structure of MOF using the device described herein. However, the device can of course assess any other material, MOF, or nano- or micro-porous materials. In addition, it is to be noted that different coating methods and conditions may be implemented for different materials.

Generally speaking, prior to the experiment, the nanoporous material was heated under vacuum to first remove any adsorbed species within the pores so as to ensure the accuracy of the measurement. The temperature was pre-selected, and then the ambient gas was introduced in a controlled manner so that equilibrium inside the high pressure cell was reached before another introduction of gas. The gas introduction was preferably controlled by shut-off valves at a constant flow rate for a pre-determined period of time, so as to determine the total volume of gas that has been introduced to the high pressure cell. The temperature and pressure inside the high pressure cell was measured once the equilibrium was reached. In the mean time, the reference and sample QCM sensors also measured the corresponding resonant frequencies before each introduction of gas and after the equilibrium was reached. After the step-wise gas introduction is completed, the gas inside the high pressure cell was evacuated. If desired, the evacuated gas can be transported to a GC/MS exit gas analyzer to determine the composition of the gas.

The use of QCM as chemical sensors had its origins in the work of Sauerbrey and King who carried out micro-gravimetric measurements in the gas phase. It was assumed in their work that a thin film applied to a thickness-shear-mode device could be treated in sensor measurements, and a shift in the resonance frequency of an oscillating AT-cut crystal could be correlated quantitatively with a change in mass added to or removed from the surface of the device. Specifically, if both the area of the crystal substrate and the density of the substance added were known, the thickness of the film could be deduced.

Sauerbrey's equation can be represented as the following:

$$\Delta m = \frac{(f_q - f)\sqrt{\rho_q \times \mu_q}}{2n \times f^2} \quad (1)$$

wherein,
- $\Delta m$ is the mass addition as a function of shift in resonant frequency ($g/cm^2$);
- $f_q$ is the resonant frequency at reference state in Hz;
- $f$ is the resonant frequency of loaded crystal in Hz;
- $\rho_q$ is the density of quartz (2.648 $g\ cm^{-3}$);
- $\mu_q$ is the effective piezoelectrically stiffened shear modulus of quartz ($2.947 \times 10^{11}\ g\ cm^{-1}s^{-2}$); and
- n is the resonant frequency mode (in this case n=1).

In order to use the Saurbrey's equation, we assume that the thin film has the same acoustic-elastic properties as the substrate. This assumption is valid by comparing the resonant frequency of the unloaded crystal with the resonant frequency of the MOF coated crystal. A common rule of thumb used is that the shift in resonant frequency due to MOF mass addition should be less than 1% for Saurbrey's equation to be used.

The frequency of QCM under high pressure can be affected by the following factors:

$$f = f_o + \Delta f_m + \Delta f_T + \Delta f_P + \Delta f_v + \Delta f_R \quad (2)$$

wherein
- $f_o$ is the fundamental resonant frequency;
- $\Delta f_m$ is the shift in frequency due to mass change;
- $\Delta f_T$ is the shift in frequency due to temperature;
- $\Delta f_P$ is the shift in frequency due to pressure;
- $\Delta f_v$ is the shift in frequency due to viscosity; and
- $\Delta f_R$ is the shift in frequency due to roughness loading.

Since all experiments were conducted under isothermal conditions, and the viscosity and roughness loading factors were negligible, the isotherm data was corrected for pressure by subtraction of the uncoated reference response from an identical QCM from the MOF-coated QCM response. We have used correction factors for temperature, pressure, but not for viscous loading as they are negligible due to the low viscosity of the gases. However we cannot currently correct for roughness loading.

The equation for pressure correction is $\Delta f_P = f_o \alpha P$ where $\alpha$ equals $1.045 \times 10^{-5}$/MPa at room temperature. A $\alpha$ has a temperature dependence of $\alpha = 1.095(10^{-5}) - 2(10^{-8})T$.

The correction for temperature is $\Delta f_T = f_o \beta T$, where $\beta$ is equal to approximately $10^{-7}$/° C. and is a function of the direction of cut of the crystal used to make the QCM. All of these effects can be canceled with a reference QCM.

The following examples are exemplary only and not intended to be unduly limiting of the various embodiments of the invention.

Example 1

FIG. 1 shows a schematic of a QCM measurement setup according to the invention. Simply speaking, the pressure chamber (aka sample chamber) contains two QCMs—a coated QCM and a reference QCM. The chamber is insulated, capable of withstanding high pressures, and is provided with a heating mantle or similar device for controlling temperature therein. A gas cylinder is fluidly connected to the chamber, and feeds gas into the chamber as needed. A pressure regulator and valves control the input of gas. Because pressure also needs to be tightly controlled, the chamber is fluidly connected to a pressure transducer and pressure relief valves. A vacuum pump is also fluidly connected thereto.

In our test experiments, the QCMs were purchased from Inficon, N.Y. They had a resonant frequency of 5 MHz, were cut at room temperature, and had polished gold electrodes on both sides. Two identical crystals were placed inside a 175 ml high pressure stainless steel cylindrical chamber with a custom-designed QCM holder. One crystal was uncoated and acted as a reference sample, while the other was coated with the material to be studied.

The sample environment chamber was constructed from stainless steel SS 316 and can be operated in a range of up to 10 bar pressure and up to 320° C. temperature. The pressure limit was determined by the range of the pressure sensor, whereas the temperature limit was due to the maximum operating temperature recommended for the O-ring (Markez® Z1213 perfluoroelastomer, size 236) used to seal the chamber at high pressure.

The two crystals were connected through four BNC connections via high-temperature-resistant cables to two phase-lock oscillators (PLO-10, Inficon, N.Y.) (not shown in FIG. 1). The output frequencies and damping voltages of both QCMs were measured by a frequency counter (Agilent® 5313X Series) and an Acquisition/Switch unit (HP 34970A) from the PLO-10 (not shown). Two K-type thermocouples (not shown) ensure that any temperature gradients were negligible.

In order to monitor the absolute pressure inside the cell, a pressure transducer (MKS 10000 Torr) was connected in the sample chamber, and the pressure was recorded by a pressure reader (PDR200) (not shown). The pressure was controlled by dosing small amounts of gas into the cell to reach each new equilibrium condition.

The temperatures, frequency changes due to the mass adsorbed and damping voltages were recorded with the LabView™ software. The sample chamber was placed inside two hemispherical heating mantles and further insulated using glass wool. A digital temperature controller (CG-15001) (not shown) was used to control the temperature with a precision of ±1° C. The gases used were research-grade and contain less than 1 ppm of water vapor.

These various additional details are omitted from FIG. 4 for simplicity, but are shown in FIGS. 5 and 6, discussed below.

Example 2

The system of the present invention is capable of measuring single-component gas adsorption under a high pressure environment. The gas was fed from the gas tank and flowed through the safety check valve and the release/leak valve before entering the high pressure cell, where the adsorption of the gas to the MOF takes place. The pressure inside the high pressure cell was monitored by the pressure sensor and was adjusted accordingly. After the isotherm measurement was completed, the gas can be exhausted either to the atmosphere or through the vacuum pump. Optionally, a volume controlling means, for example a flow meter (not shown), is connected to an inlet (not shown) of the high pressure cell in order to control the amount of gas being introduced.

The pressure cell shown in the schematic is a cylindrical chamber of a volume of 170 cm$^3$. The QCMs used in this experiment were room temperature cut QCM. For this experiment, a reference QCM and a MOF coated QCM were inserted into the pressure cell. The reference QCM was used to correct for the effects of the bulk phase on the QCM and hence obtain only the excess adsorption in the MOF. The quality of the $CO_2$ gas used as an analyte in this experiment were of research grade having <1 ppm of moisture or $N_2$.

Example 1A

Prior to conducting these experiments, SEM images and XRD patterns of the MOF-coated samples were obtained and shown in FIG. 2A-2F. These characterizations confirm that the MOF particles were indeed dispersed on the surface of the QCM and that they retain the expected crystal structure.

The CuBTC(HKUST-1) sample was deposited on INFI-CON AT-cut quartz at 25° C. The sample was preheated at 120° C. for 9 hours, followed by forced convection cooling to 21° C.

The results of two experimental adsorption and desorption under high pressure, as well as corresponding Langmuir adsorption and desorption isotherm curves, are shown in FIG. 3A for CuBTC(HKUST-1). The experimental procedure began with initial preheating of the pressure cell with the MOF coated QCM and reference uncoated QCM to a temperature of 105° C. at a pressure of 0.59 psi to remove the moisture present in the MOFs. The system, however, is capable of attaining even higher temperatures. Since the MOFs were deposited by self assembled monolayers on the gold surfaces of the QCM, the possibility of detachment of the MOFs from the QCM limited the initial preheating temperature to 105° C.

Following the initial preheating, adsorption and desorption isotherms for carbon dioxide were collected after cooling the pressure cell to 21° C. The isotherms were collected between 0.6 psi to 55 psi though higher pressures are also attainable. These isotherms were cycled twice to demonstrate the repeatability of the measurement. From these isotherms the important thermodynamic property of the HKUST-1 MOF, heat of sorption for both adsorption and desorption was calculated to be −19.2 kJ/mol, which agrees with the literature.

Example 1B

The Cu-hifbb MOF crystals were deposited on the QCM by spin-coating at 150 rpm. Following this they were prebaked at 190° C. for 30 min. These QCMs were then inserted into the pressure cell and preheated to 185° C. at low vacuum over night.

Following the initial preheating the adsorption isotherms were obtained for $CO_2$, $N_2$ and $CH_4$ at temperatures 30° C., 50° C. and 70° C. for pressures ranging from 0.2 psi to 100 psi. From these isotherms the thermodynamic properties of the Cu-hifbb crystals were obtained by performing a global fit with the experimental data and are listed in Table 1. The adsorption isotherms are presented in FIG. 3B along with the gas analyzer data for $CO_2$ at 25° C.

Example 1C

The ZIF 90 crystals were deposited on the QCM by drop-coating. Following this they were prebaked at 185° C. for 30 min. The QCMs were then inserted into the pressure cell and preheated to 185° C. at low vacuum overnight.

Following the initial preheating the adsorption isotherms were obtained for $CO_2$ at 30° C., 50° C. and 70° C. for pressures ranging from 0.2 psi to 100 psi. From these isotherms the thermodynamic properties of the ZIF 90 crystals with respect to $CO_2$ were obtained by performing a global fit with the experimental data and are listed in Table 2. The $CO_2$ adsorption isotherms are presented in FIG. 3C.

Example 1D

Matrimid® was deposited by spin-coating a 10% wt suspension of Matrimid® in N-Methylpyrollidone. These QCMs were preheated to a temperature of 120° C. at low vacuum overnight.

Following the initial preheating the adsorption isotherms were obtained for $CO_2$ at 25° C., 42° C. and 53° C. for pressures ranging from 0.2 psi to 60 psi and for $CH_4$ at 29° C. for pressures ranging from 0.2 psi to 35 psi. From these isotherms the thermodynamic property of the Matrimid® with respect to $CO_2$ and $CH_4$ was obtained by performing a global fit with the experimental data and are listed in Table 3. The adsorption isotherms are presented in FIG. 3D and compared with the literature data. The adsorption isotherm were then fit with dual mode adsorption model given by $$C = K_D \times P + \frac{C_H \times \alpha P}{1 + \alpha P} \quad (3)$$

$$\alpha = \alpha_0 \times e^{\left(\frac{-\Delta H_a}{RT}\right)}$$

where C is the penetrant concentration, $K_D$ is the Henry's law constant(function of Temperature), $C_H$ is the Langmuir Capacity Constant, $\alpha$ is the Langmuir affinity Constant (function of temperature), P is the gas pressure, $\Delta H_a$ is the Heat of Adsorption (kJmol$^{-1}$), $\alpha_0$ is the temperature independent Langmuir affinity constant, R is the Universal gas constant (8.314 kJmol$^{-1}$K$^{-1}$) and T is the Gas Temperature (K).

As shown in FIG. 3A-3D, the system of the present invention can measure the gas adsorption and desorption in a manner that closely follows the Langmuir adsorption model, even under high pressure. These results clearly demonstrate that the present invention successfully combines a QCM sensor under a high pressure environment for measuring gas adsorption onto a nanoporous material coated on the QCM sensor.

FIG. 3A-D shows the number of grams of gas adsorbed per unit area of the MOF film as a function of absolute pressure, as measured by the capacitive pressure sensor. The data is shown as individual points, whereas the line is the fit to the Langmuir equation, as follows:

$$\Delta m = \frac{K\alpha_0 e^{-\frac{\Delta H}{RT}} P}{1 + \alpha_0 e^{-\frac{\Delta H}{RT}} P} \quad (4)$$

where K is a constant related to the adsorption capacity of the film, P is the pressure of the gas, R is the ideal gas constant, T is the absolute temperature, alpha zero is Langmuir affinity constant and delta H is the heat of adsorption for that gas in the film.

TABLE 1

Thermodynamic properties of Cu-hifbb crystals based on adsorption isotherms

| Parameters | $C_H$ (cc/g) | $\alpha_0$ (psi$^{-1}$) | $\Delta H_a$ (kJmol$^{-1}$) |
|---|---|---|---|
| $CO_2$ | 24.1 ± 0.8 | 20.3e−06 | −21.3 |
| $CH_4$ | 25.4 ± 0.4 | 56.3e−06 | −16.1 |
| $N_2$ | 37.8 ± 0.1 | 33.4e−06 | −12.4 |

TABLE 2

Thermodynamic properties of ZIF 90 crystals based on adsorption isotherms

| Parameters | $C_H$ (cc/g) | $\alpha_0$ (psi$^{-1}$) | $\Delta H_a$ (kJmol$^{-1}$) |
|---|---|---|---|
| $CO_2$ | 84.3 ± 1.8 | 2.5e−08 | −33.4 |

TABLE 3

Thermodynamic properties of Matrimid based on adsorption isotherms

| Parameter | $C_H$ (cc/cc) | $\alpha_0$ (1/psi) | $K_D$ (cc/cc · psi) | $\Delta H_a$ (kJmol$^{-1}$) |
|---|---|---|---|---|
| $CO_2$ | 37 ± 0.5 | 1.7e−07 | 0.01 | −30.6 |
| $CH_4$ | 4 ± 0.01 | 2.5e−06 | 0.07 | −24.4 |

The present data were found to be in good agreement with the literature, and minor quantitative are possibly due to differences in polymer film casting techniques, effects of physical aging of the polymer, and differences in penetrant gas purity. However, it is clear that the QCM-based measurements demonstrate an overall good agreement with data obtained by conventional gravimetric techniques.

Example 3

The system of the present invention can also be used in a binary gas system. FIG. 4 shows another embodiment capable of detecting gas adsorption in a binary-gas system, and the detail of the high pressure cell chamber is illustrated in FIG. 5A-5C. Detailed and enlarged illustration of each step, including gas intake, thermocouple fitting, pressure gauge fitting, GC/MS exit gas analyzer, gas feed valve, alternative pressure gauge fitting, and exit gas analyzer are provided in FIG. 6A to 6G, and will be discussed below. The detailed specifications of the components in these figures are exemplary only, and can be modified as needed.

In FIG. 4, two 5 MHz quartz crystal microbalances are placed inside a stainless steel high pressure chamber. The temperature and pressure of the high pressure chamber were monitored by thermocouple and pressure transducer, respectively. One of the two quartz crystal microbalances sensor was coated with the nanoporous material, in this embodiment HKUST-1 mentioned above, and the other one was not coated (except for the gold electrodes required to monitor its frequency of vibration) and serves as a reference QCM. This system is capable of measuring the simultaneous adsorption and desorption of several gases in a mixture.

Unlike the single gas system, the multiple gas system mentioned in this example has a smaller bulk volume above the QCM, and is connected to an exit gas analyzer system (GC/MS or infra absorption) to determine the compositional change of gas mixture from the sample cell. Since the compositional change upon adsorption/desorption needs to be measured, and since the amount of sample on the QCM crystal is very small, the total volume of the gas above the sample also must be very small in order for the compositional analysis system to be able to measure a significant change in composition.

As mass loading changes due to ambient gas adsorption on the coated QCM sensor, frequency of the QCM sensor changes accordingly. The pressure inside the high pressure chamber is increased slowly, and the temperature, pressure, and mass adsorbed (deduced from the equations above) are recorded when each new equilibrium is reached. The reference QCM sensor also responds to changes in temperature and pressure. Because both the coated and uncoated QCM sensors respond to pressure and temperature in the same manner, the mass accumulated into the nanoporous material on the coated QCM sensor can be calculated by means of comparing the frequency change of the coated QCM sensor with that of the uncoated QCM sensor.

The pressure exemplified herein ranges from a few millitorr up to 8 bar pressure. However, other pressure ranges are also contemplated by the present inventors and can be implemented without deviating from the spirit of the present invention, provided that the components of the device are rated for the desired pressures.

The temperature experimented in the present invention ranges from room temperature up to 185° C. However, other temperature ranges are also contemplated by the present inventors and can be implemented without deviating from the spirit of the present invention. For example, the use of O-rings with higher temperature rating will allow the device to be used at higher temperatures than demonstrated herein.

Referring to FIG. 5A, where the chamber head of the high pressure cell of the present invention is illustrated. The chamber head comprises two sets of instruments, each comprising a gas inlet for providing gas into the chamber, a thermocouple for measuring and monitoring the temperature, a gas outlet for evacuating the chamber after the measurement is completed, and a pressure gauge for measuring and monitoring the pressure inside the chamber. The dimensions of each component illustrated in FIG. 5 are for reference only, and can be modified depending on the materials being assessed.

Referring to FIG. 5B, where the chamber bottom of the high pressure cell of the present invention is illustrated. Two quartz crystal microbalance sensors are provided. One of the quartz crystal microbalance sensors is coated with HKUST-1, in a manner aforementioned, and serves as a sample sensor. The other quartz crystal microbalance sensor is not coated and serves as a reference sensor.

Referring to FIG. 5C, which is a cross-sectional view of the chamber bottom shown in FIG. 5B along the broken line. Assuming the air gap above and below the sample QCM to be 0.5 mm, the total sample volume to be calculated is about 0.5078 cm$^3$, including the dead volume in the inlet valves, pressure gauges, exit gas analyzer and electrical connections. For this volume, assuming a 50:50 concentration of $CO_2$ and $CH_4$ at STP, the total mass of gas in this sample cell volume is 0.684 mg, corresponding to 22.8 μmoles. The number of moles is the mass of gas divided by the molecular weight. For a 50% mixture of $CO_2$ and $CH_4$, the average of the two molecular weights was used.

The reference and sample QCM sensors are connected to a computer through SMB (sub-miniature B coaxial feedthroughs) connections to read and record the measured resonant frequencies therefrom. Then, the mass added to the sensors through gas adsorption can be calculated by equations (1) and (2) provided above. The total number of moles, $M_0$ is the sum of the moles for each component $M_1$ and $M_2$. After the experiment the total number of moles in the gas is calculated, $M_3$, based upon the pressure and internal cell volume. The composition by mole fraction analyzed for a small sample extracted from the cell. For example, if the result is a mole fraction: $X_1$ and $X_2$, then the number of moles in the gas for each component is $X_1 \times M_3$, and $X_2 \times M_3$, so the amount of gas in the film is the difference as follows:

$$dM_1 = M_1 - X_1 \times M_3 \text{ and } dM_2 = M_2 - X_2 \times M_3 \tag{5}$$

FIG. 6A shows the gas feed design corresponding to FIG. 4 for providing a gas to both the reference QCM sensor and the sample QCM sensor. The four-way connector functions to divert the gas from gas source to the reference QCM sensor or the sample QCM sensor. The specifications of the various components in FIG. 6A-G are for reference only, and can be modified depending on varied.

FIG. 6B shows the thermocouple fitting to the reference QCM sensor and the sample QCM sensor. A K-type Chromega-Alomega 304 SS Sheath 1/16" thermocouple is used in this configuration. However, thermocouples of different types and/or diameters may also be used, depending on the design and other relevant parameters, without deviating from the spirit of the present invention.

FIG. 6C shows the pressure gauge fitting to the reference QCM sensor and the sample QCM sensor, in order to measure the pressure inside the high pressure cell before and after the isothermal equilibrium is reached. After the adsorption experiments have been completed, the response of the reference QCM is subtracted from the sample deposited QCM to determine the actual adsorption in the MOF, correcting for pressure and temperature effect on the QCM. In this embodiment, a pressure transducer capable of measuring the range between 1 to 250 psi is used to detect the pressure inside the high pressure cell and to convert the reading to an electrical signal. The pressure transducer is optionally connected to a signal conditioner to condition the electrical signal output from the pressure transducer. The optional signal conditioner is in turn connected to a computer to read and record the pressure inside the high pressure cell. It is to be noted that other pressure transducers/sensors capable of measuring a different range of pressure can also be used in the present invention without deviating from the spirit of the present invention.

FIG. 6D shows the configuration of exit gas analyzer connected to the high pressure cell. The gas flowed from the high pressure cell is extracted by a GC/MS feed pump, which in turn connects to a three way connector. Thereafter, the extracted gas is either directed to a GC/MS exit gas analyzer to analyze the content of the gas, or exhausted to the atmosphere.

FIG. 6E shows the selection of tubes and adaptors between the shut off valve connected to the four-way connector and pressure transducer.

FIG. 6F shows the selection of tubes and adaptors between the pressure transducer and the reference/sample QCM sensors in the high pressure cell.

FIG. 6G shows the selection of tubes and adaptors between the gas outlet of the high pressure cell and the shut-off valve connected to the GC/MS exit gas analyzer shown in FIG. 6D.

The exact configuration and sizes described in FIGS. 5 and 6 can be modified according to maximum temperature and pressure needs, and according to sample size and availability of components. However, the device shown illustrates one working embodiment of the invention.

What is claimed is:

1. An apparatus for measuring mass change under high pressure, comprising:
   a high pressure cell comprising a reference quartz crystal microbalance sensor and a sample quartz crystal microbalance sensor, wherein the sample quartz microbalance sensor is coated with a test sample selected from the group consisting of nanoporous materials and metal-organic frameworks;
   a pressure sensor operatively connected to the high pressure cell;
   a thermocouple operatively connected to the high pressure cell, wherein the high pressure cell is maintained at a pre-selected temperature;
   a gas inlet fluidly connected to the high pressure cell; and
   a gas outlet fluidly connected to the high pressure cell.

2. The apparatus of claim 1, further comprising an analyzer fluidly connected to the gas outlet for determining the quantity of gas within the high pressure cell.

3. The apparatus of claim 2, wherein the analyzer is selected from the group consisting of fourier transform infrared spectrometer (FTIR), gas chromatograph (GC), mass spectrometer (MS), gas chromatograph/mass spectrometer (GC/MS) and high-pressure liquid chromatograph (HPLC).

4. The apparatus of claim 1, wherein the nanoporous material is CuBTC, Cu-hifbb, ZIF 90 crystal, $Zn_4O(BTB)_2$, $Zn_4O(BDC)_3$, $Mn_3[(Mn_4Cl)_3(BTT)_8]_2$ or $Cu_3(BTC)_2(H2O)_3$.

5. The apparatus of claim 1, where in the nanoporous material is CuBTC, Cu-hifbb, or ZIF 90 crystal.

6. The apparatus of claim 1, wherein a flow meter is operatively connected to the gas inlet for controlling a volume of gas to be introduced to the high pressure cell.

7. The method of claim 1, wherein the test sample is a nanoporous material.

8. The apparatus of claim 1, wherein the test sample is a metal organic framework.

9. The apparatus of claim 1, wherein the metal organic framework is HKUST-1, $Cu(hfipbb)(H_2hfipbb)_{0.5}$ or as-synthesized ZIF-90 crystals.

10. A method for measuring gas adsorption or desorption to a test sample under high pressure, comprising:
   a) providing an apparatus comprising:
      i) a high pressure cell comprising a reference quartz crystal microbalance sensor and a sample quartz crystal microbalance sensor, wherein the sample quartz crystal microbalance sensor is coated with a test sample selected from the group consisting of nanoporous materials and metal-organic frameworks;
      ii) a pressure sensor operably connected to the high pressure cell;
      iii) a thermocouple operably connected to the high pressure cell, wherein the high pressure cell is maintained at a pre-selected temperature;
      iv) a gas inlet fluidly connected to the high pressure cell; and
      v) a gas outlet fluidly connected to the high pressure cell;
   b) measuring at a first state, a first temperature from the thermocouple and a first pressure from the pressure sensor;
   c) measuring at the first state, a first reference resonant frequency from the reference quartz crystal microbalance sensor and a first sample resonant frequency from the sample quartz crystal microbalance sensor;
   d) preheating a gas to about the pre-selected temperature;
   e) introducing the gas to the high pressure cell through the gas inlet at about the pre-selected temperature;
   f) measuring at a second state, a second temperature from the thermocouple and a second pressure from the pressure sensor;
   g) measuring at the second state, a second reference resonant frequency from the reference quartz crystal microbalance sensor and a second sample resonant frequency from the sample quartz crystal microbalance sensor; and
   h) determining a mass of the gas adsorbed to the test sample coated to the sample quartz crystal microbalance sensor based on difference of mass addition between the reference quartz crystal microbalance sensor and the sample quartz crystal microbalance sensor.

11. The method of claim 10, wherein the step of determining the mass of the gas adsorbed to the nanoporous material is performed by subtracting a mass addition to the reference quartz crystal microbalance sensor from a mass addition to the sample quartz crystal microbalance sensor, wherein the mass addition to the reference and sample quartz crystal microbalance sensors is determined by the following formula:

$$\Delta m = \frac{(f_q - f)\sqrt{\rho_q \times \mu_q}}{2n \times f^2}$$

wherein
   $\Delta m$ is the mass addition to the sample quartz crystal microbalance sensor (g/cm$^2$);
   $f_q$ is the resonant frequency at the first state in Hz;
   $f$ is the resonant frequency at the second state in Hz;
   $\rho_q$ is the density of quartz, 2.648 g·cm$^{-3}$;
   $\mu_q$ is the effective piezoelectrically stiffened shear modulus of quartz, 2.947×10$^{11}$ g·cm$^{-1}$·s$^{-2}$; and
   n is the resonant frequency mode.

12. The method of claim 11, wherein f is determined by the following formula:

$$f = f_o + \Delta f_m + \Delta f_T + \Delta f_P + \Delta f_v + \Delta f_R$$

wherein,
   $f_o$ is a fundamental resonant frequency;
   $\Delta f_m$ is a shift in frequency due to mass change;
   $\Delta f_T$ is a shift in frequency due to temperature;
   $\Delta f_P$ is a shift in frequency due to pressure;
   $\Delta f_v$ is a shift in frequency due to viscosity; and
   $\Delta f_R$ is a shift in frequency due to roughness loading.

13. The method of claim 12, wherein $\Delta f_P = f_o \alpha P$, and $\alpha = 1.095(10^{-5}) - 2(10^{-8})$ T·MPa$^{-1}$.

14. The method of claim 12, wherein $\Delta f_T = f_o \beta T$, and $\beta$ is equal to approximately $10^{-7}$/°C.

15. The method of claim 10, wherein the test sample is a nanoporous material.

16. The method of claim 10, wherein the nanoporous material is CuBTC, Cu-hifbb, or ZIF 90 crystal.

17. The method of claim 10, wherein the gas introduced to the high pressure cell has two or more components.

18. The method of claim 17, wherein the high pressure cell has a small cell volume, and an analyzer is connected to the gas outlet for determining a quantity of gas within the high pressure cell.

19. The method of claim 10, wherein the test sample is a metal organic framework.

20. The method of claim 10, where in the nanoporous material is CuBTC, Cu-hifbb, ZIF 90 crystal, $Zn_4O(BTB)_2$, $Zn_4O(BDC)_3$, $Mn_3[(Mn_4Cl)_3(BTT)_8]_2$, or $Cu_3(BTC)_2(H_2O)_3$.

21. The method of claim 10, wherein the metal organic framework is HKUST-1, Cu(hfipbb)(H$_2$hfipbb)$_{0.5}$ or as-synthesized ZIFF-90 crystals.

22. The method of claim 10, wherein the gas introduced to the high pressure cell has two or more components selected from the group consisting of H$_2$, CH$_4$, CO$_2$, CO, H$_2$O, N$_2$ and other small gases.

* * * * *